United States Patent [19]

Sawai et al.

[11] 4,208,185

[45] * Jun. 17, 1980

[54] METHOD AND APPARATUS FOR THE MEASUREMENT OF ANTIGENS AND ANTIBODIES

[75] Inventors: Masanobu Sawai, Yamato; Tadamitsu Sudo, Sagamihara; Shogo Enomoto, Tokorozawa, all of Japan

[73] Assignee: Mitsubishi Chemical Industries Limited, Tokyo, Japan

[*] Notice: The portion of the term of this patent subsequent to Oct. 3, 1995, has been disclaimed.

[21] Appl. No.: 917,258

[22] Filed: Jun. 20, 1978

Related U.S. Application Data

[63] Continuation-in-part of Ser. No. 825,160, Aug. 16, 1977, Pat. No. 4,118,192.

[30] Foreign Application Priority Data

Aug. 16, 1976 [JP] Japan .................................. 51/97158
Feb. 15, 1978 [JP] Japan .................................. 53/15328

[51] Int. Cl.$^2$ ...................... G01N 21/24; G01N 33/16
[52] U.S. Cl. .................................. 23/230 B; 356/246; 422/57; 424/12; 435/7
[58] Field of Search ...................... 23/230 B; 424/12; 195/103.5 A; 356/105, 246; 422/55, 56, 57

[56] References Cited

U.S. PATENT DOCUMENTS

| | | | |
|---|---|---|---|
| 3,984,533 | 10/1976 | Vzgiris | 23/230 B |
| 4,011,044 | 3/1977 | Uzgiris | 23/230 B |
| 4,118,192 | 10/1978 | Sawai et al. | 195/103.5 A |

FOREIGN PATENT DOCUMENTS

2749956 5/1978 Fed. Rep. of Germany .
1384399 2/1975 United Kingdom .

OTHER PUBLICATIONS

R. J. Cohen, Immunochemistry, 12, pp. 349-351, (Apr. 1975).

*Primary Examiner*—R. E. Serwin
*Attorney, Agent, or Firm*—Oblon, Fisher, Spivak, McClelland & Maier

[57] ABSTRACT

A method of the quantitative measurement of antigens and antibodies by reacting antibody- or antigen-sensitized insoluble carrier particles with a corresponding antigen or antibody or a mixture thereof in a sample and irradiating the reaction mixture with light of a specific wavelength to measure the absorbance or percent absorption of the reaction mixture, and an apparatus for use therein.

31 Claims, 14 Drawing Figures

METHOD AND APPARATUS FOR THE MEASUREMENT OF ANTIGENS AND ANTIBODIES

CROSS-REFERENCE TO RELATED APPLICATIONS

This application is a continuation in part of application Ser. No. 825,160 filed Aug. 16, 1977, now U.S. Pat. No. 4,118,192.

BACKGROUND OF THE INVENTION

1. Field of the Invention

This invention relates to a method and apparatus for the measurement of antigens and antibodies. More particularly, this invention relates to a method of the quantitative measurement of antigens and antibodies by supporting an antibody or an antigen on insoluble carrier particles having minute particle diameters to sensitize the insoluble carrier particles, then reacting the sensitized carrier with a corresponding antigen, antibody or mixture thereof and irradiating the reaction mixture with light of a specific wavelength to measure the absorbence or percent absorption of the reaction mixture, and an apparatus for use therein.

2. Description of the Prior Art

There is a continuing need for rapid, accurate, qualitative and quantitative determinations of biologically active substances, e.g., antigens, antibodies, at extremely low concentrations. Today, there is a wide need for determining the presence of drugs in body fluids. In addition, in medical diagnosis, it is frequently important to know the presence of various substances which are synthesized naturally by the body or ingested.

Heretofore it has been known to detect antibodies or antigens semiquantitatively by reacting latex particles on which an antibody or an antigen has been supported with a corresponding antigen or antibody on a glass plate and observing visually the agglutination.

In recent years, it was proposed in the following articles to quantitatively determine antigens and antibodies using the above-mentioned latex particles by supporting an antibody or antigen on the latex particles to sensitize them, reacting the supported antibody or antigen with a corresponding antigen or antibody to be determined to agglutinate the latex particles, and measuring the rate of decrease in turbidity of the supernatant of the latex by means of visible lights for the determination of the antigen or antibody utilizing the agglutination phenomena of the latex reagent:

(A) CROATICA CHEMICA ACTA, 42, (1970), p.p. 457–466; and
(B) European Journal of Biochemistry, Vol. 20, No. 4, (1971), p.p. 558–560.

Since the method of the above proposal utilizes the measurement of rate of decrease in turbidity to determine the antigen or antibody, it is necessary to use an antibody- or antigen-sensitized latex of an extremely low concentration, for example, in the range of 0.007 to 0.028%, to carry out the reaction of the latex and the antigen or antibody in a stationary state, to remove any impurity capable of affecting the turbidity from the sample, and the like. As a result, the above-mentioned method is disadvantageous in that the rate of the antigen-antibody reaction is inevitably decreased, both the precision and the reproducibility are insufficient for the determination technique of antigens or antibodies, and that the removal of impurities sometimes requires extremely complicated operations. Accordingly it is difficult to apply the above method to the determination of such antigens as fibrinogen (Fg), human chorionic gonadotropin (hCG) and the like, since they require complicated procedures for the preparation of their reagents and they are difficult to cause reproducible agglutination reactions if they are present in blood or urine which additionally contains various other substances capable of adversely affecting the reaction.

Also in the article, (C) Immunochemistry, Vol. 12, p.p. 349–351 (1975)

it was proposed to determine quantitatively antibodies and antigens by irradiating the above-mentioned agglutinated latex particles with a laser beam and measuring the change in width or spectral lines of the scattered light of the laser beam in order to determine the mean diffusion constant ($\overline{D}$) which gives an indication of the Brownian motion of the agglutinated particles which in turn is inversely proportional to the size of the agglutinated particles. Also in this method, since the antibody- or antigen-sensitized latex is used in an extremely low concentration, for example, as low as 0.001%, the rate of the antigen-antibody reaction is so decreased that both the precision and the reproducibility become poor. In addition, this method is also disadvantageous in that it requires complicated calculation using the technique of spectrum analysis which in turn requires complicated operations, and that any impurity in the sample must be removed prior to the measurement. Accordingly, this method has not been put into practice as well. The above paper C also describes that determination by the turbidity method as reported in the foregoing paper A gives extremely imprecise results (FIG. 2 on page 350 of the same).

SUMMARY OF THE INVENTION

Accordingly, it is an object of the invention to provide a method and apparatus for the rapid determination of an antibody and/or antigen in a sample to be tested with high precision and good reproducibility.

It is another object of this invention to provide a method and apparatus for rapidly detecting whether the concentration of an antibody or antigen in a sample is higher or lower than a certain level, using an extremely small amount of the sample.

It is a still another object of this invention to provide a method and apparatus for determining an extremely slight amount of an antigen and/or antibody which could heretofore be determined practically only by radioimmunoassay (RIA), with a precision equal to or higher than that of RIA and much more rapidly and safely.

It is a further object of this invention to provide a method for the quantitative determination of antigens capable of determining not only multivalent antigens but incomplete antigens such as, for example, haptens.

It is a still further object of this invention to provide a method for determining antibodies and/or antigens using not only the agglutination reaction of the antibodies and/or antigens but the agglutination inhibition reaction thereof.

Briefly, these and other objects and advantages of this invention, as will hereinafter be made clear from the ensuring discussion, can be attained by supporting an antibody or an antigen on insoluble carrier particles with an average diameter of not greater than 1.6 microns to sensitize the insoluble carrier particles, reacting the supported antibody and/or antigen with a corresponding antigen or antibody or a mixture thereof to be determined in a liquid medium and irradiating the resulting reaction mixture with light having a wavelength in the range of 0.6 to 2.4 microns and longer than the average diameter of said carrier particles by a factor of at least 1.1 to measure the absorbance or percent absorption of the reaction mixture (exclusive of the case where the reaction mixture is irradiated with the light having a wavelength longer than the average diameter of the carrier particles by a factor of at least 1.5 to measure the absorbance of the reaction mixture).

BRIEF DESCRIPTION OF THE DRAWING

In FIG. 4. 1: light source, 2: filter, 3: sample cell, 4: reference cell, 5 and 6: photocells, 7: amplifier and 8: recorder

DETAILED DESCRIPTION OF THE PREFERRED EMBODIMENTS

Figure 1:
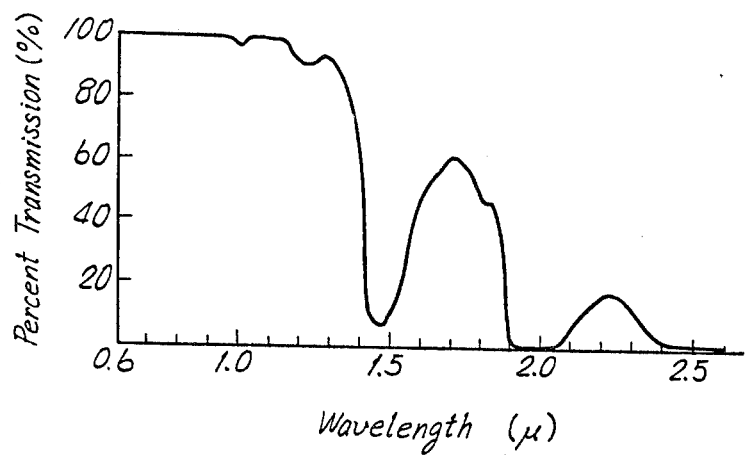
FIG. 1 is a chart of the absorption spectra of water measured at wavelengths of the applied light in the range of 0.6 to 2.4 microns using an absorption cell with a thickness of 1 mm.

As previously described, the prior art method wherein the degree of agglutination caused by bringing antibody- or antigen-sensitized latex particles into contact with a sample containing an antigen or an antibody is measured by the rate of decrease in turbidity of the supernatant of the latex, involves various disadvantages such as poor precision and reproducibility, since the reaction has to be carried out in a standing state with an extremely dilute latex.

Also in this prior art method, it is necessary to previously remove any impurity in the sample which may affect the turbidity.

Thus, it is a matter of course that in order to determine an antigen and/or an antibody in a sample with high precision and good reproducibility, an antibody- or antigen-sensitized insoluble carrier, for example, latex particles should desirably be contacted at as high a concentration as possible with the sample which contains an antigen and/or antibody capable of reacting with the supported antibody or antigen and in order to accelerate the antigen-antibody reaction caused thereby, this reaction should desirably be carried out under agitation, not in a standing state.

We have now found that, in order to carry out an antigen-antibody reaction between an antibody or antigen supported on insoluble carrier particles and a corresponding antigen or antibody in a sample at as high a concentration of the latex as possible under non-standing conditions and at the same time to detect quantitatively the degree of this reaction, it is remarkably effective:

(1) to use an insoluble carrier having an average particle diameter of not greater than 1.6 microns,
(2) to irradiate the antigen-antibody reaction mixture with light having a wavelength in the range of 0.6 to 2.4 microns and longer than the average diameter of the carrier particles by a factor of at least 1.1; and
(3) to measure the absorbance or percent absorption of the reaction mixture.

The reason is that the degree of the antigen-antibody reaction in the presence of the sensitized insoluble carrier particles correlates very closely to the intensity of the transmitted light. It is apparent that the degree of the antigen-antibody reaction also correlates to the amount (or concentration) of the antibody and/or antigen in the sample as long as the reaction is carried out under specifically determined conditions. The above-mentioned method according to this invention, therefore, enables rapid determination of an antibody and/or antigen in a sample with an extremely high precision by a technique quite different from the measurement of turbidity or mean diffusion constant as in the prior art methods. The light of a wavelength in the range of 0.6 to 2.4 microns which is used in this invention is in the near infrared region or in a portion of the visible region which is closely adjacent to the near infrared region. Of these regions, the light used in accordance with the invention has preferably a wavelength in the near infrared region of 0.8 to 1.8 microns, more preferably 0.9 to 1.4 microns.

Heretofore the technique of spectrum analysis using light in the infrared region of a wavelength of at least 2.5 microns or light in the ultraviolet region of a wavelength of not greater than 0.4 micron is known as a method for investigating molecular structures or characteristics thereof. The light in the near infrared or the adjacent visible region which is used in this invention and which may hereinafter be referred to as "light in the near infrared region" for the sake of convenience, however, have heretofore been considered to have only limited uses and therefore attracted little attention.

According to our investigation, it has been found that the above-mentioned light in the near infrared region in principle possesses eligibility as the light to be used in this invention, since it is transmitted very well by aqueous media such as water, aqueous solutions and the like which are used most generally as the basal media for the antigen- or antibody-containing samples such as water, sera, urine, salt solutions, etc., as well as, as the basal media for the above-mentioned latices, and among the near infrared light, particularly rays of wavelengths of 0.8 to 1.4 microns and those of 1.53 to 1.88 microns are absorbed by the aqueous media only to a very little extent. In addition it has been found that, when the reaction mixture obtained by reacting the foregoing antibody- or antigen-sensitized insoluble carrier particles having an average diameter of not greater than 1.6 microns, preferably 0.1 to 1 micron with an antigen and/or antibody in a sample to cause agglutination is irradiated with a light in the above-mentioned near infrared region having a wavelength longer than the average diameter of the carrier by a factor of at least 1.1, preferably at least 1.5 in accordance with the invention, the absorbance or percent absorption of the reaction mixture correlates very closely to the degree of the agglutination resulting from the antigen-antibody reaction. As previously mentioned, this invention excludes the case where the reaction mixture is irradiated with the light having a wavelength longer than the average diameter of the carrier particles by a factor of at least 1.5 to measure the absorbance of the reaction mixture.

The term "percent absorption" used herein is defined by the equation:

$$S = \frac{I_o - I}{I_o} \times 100 \, (\%) \quad (1)$$

wherein S represents the percent absorption, $I_o$ represents the intensity of the transmitted light when the cell contains the same system as the reaction mixture, except for the absence of the antigen and/or antibody to be measured, and I represents the intensity of the transmitted light when the cell contains the reaction mixture.

As is apparent from the above definition, the percent absorption used herein may be referred to in another way as the percentage of attenuated or not transmitted light. Since the percent absorption correlates to absorbance (A) which can be measured by means of a conventional spectrophotometer, for example, for use in infrared spectrometry, it may be expressed in terms of absorbance for the sake of convenience.

In the infrared spectrometry, absorbance (A) is defined by the equation:

$$A = \log I_o/I \quad (2)$$

wherein $I_o$ and I have the same meanings as in Equation 1. Thus, it is possible to determine antigens and antibodies by the measurement of either parameter of percent absorption defined by Equation 1 or absorbance by Equation 2. In either course, the results will coincide with an acceptable deviation, as long as the measurement is carried out properly.

In brief the above-mentioned percent absorption (S) or absorbance (A) relates to the relative ratio of $I_o/I$. If the basal medium of the sample is a transparent liquid medium, the measurement of $I_o$ may conveniently be performed with only the suspension containing the antibody- or antigen-sensitized insoluble carrier particles, said suspension having been diluted with, for example, water to the same concentration as that in the mixture.

By the way, percent transmission spectrum in the range of 0.6 to 2.4 microns of a water layer 1 mm in thickness is shown in FIG. 1, wherein the abscissa indicates the wavelength of light and the ordinate the percent transmission of the light. It can be seen from FIG. 1 that the lights of wavelengths in the range of 0.6 to 1.4 microns are transmitted by water without substantial absorption by the water which is employed most widely as the basal media for latices and samples, and that the lights of wavelengths in the range of 1.53 to 1.88 microns are also considerably transmitted by water so that light of a wavelength in these ranges can be utilized in principle in the practice of this invention. Also, it is apparent from FIG. 1 that the lights of wavelengths in the range of 2.1 to 2.35 microns are also transmitted by water in the order of 20%, and therefore it should be understood that the rays of such wavelengths can be used in conjunction with a highly sensitive photometer, although they are rather not preferred.

Figure 2:
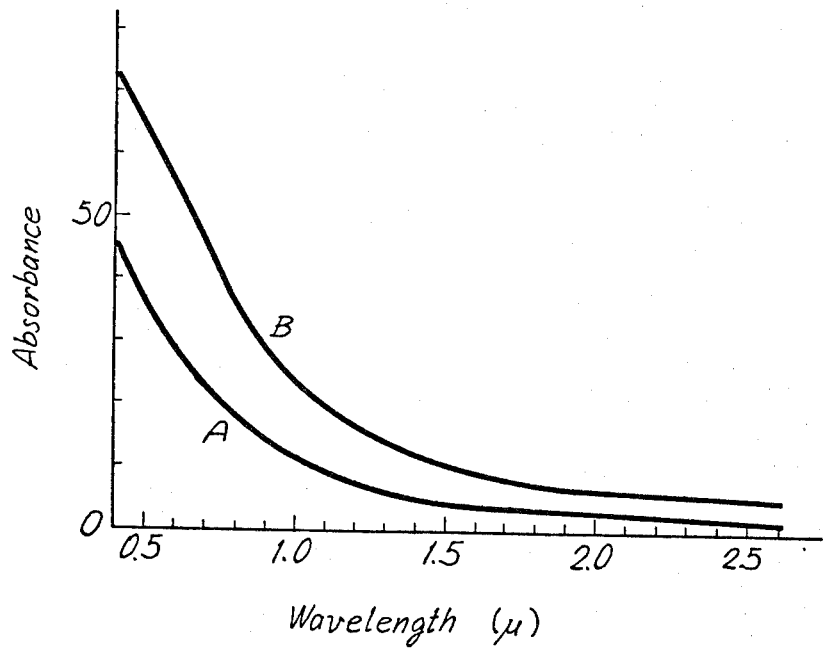
FIG. 2 is a graph which shows the change of percent absorption with particle diameter of polystyrene latex.

FIG. 2 shows the relationship between the absorbance of a polystyrene latex (1% solids content by weight) in the ordinate and the wavelength of light in microns in the abscissa when a cell of 2 mm in thickness is used. In FIG. 2, Curve A denotes the change in absorbance of a polystyrene latex in which the average diameter of the particles is 0.481 micron and Curve B denotes that of a polystyrene latex in which the average diameter is 0.804 micron. In the determination of absorbance, the latex was diluted for the convenience of the measurement, and the absorbance of the latex was evaluated by multiplying the actually obtained value of absorbance by the dilution factor.

As will be understood from FIG. 2, the absorbance of the latex is so significantly increased with the lights of wavelengths less than 0.6 micron that it is quite difficult to measure the change in percent absorption of an antigen-antibody reaction mixture using a light of such a wavelength, whereas with the lights of wavelengths of at least 0.8 micron, particularly at least 1 micron, the absorbance of the latex itself is relatively small so that light of a wavelength of at least 0.8 micron, preferably at least 1 micron is suitable for the above-mentioned measurement of percent absorption of such reaction mixture.

When Curve A is compared with Curve B in FIG. 2, it is recognized that the absorbance of the polystyrene latex increases with increasing average diameter of the polystyrene particles. Accordingly it would also be understood that those latex particles having an excessively large average diameter are unfavorable for the method of this invention.

In accordance with our investigation, it has been found that the insoluble carrier particles useful for this invention must have an average particle diameter of not greater than 1.6 microns and that those latex particles having an average diameter of 0.1 to 1 micron, preferably 0.2 to 0.8 micron are suitable.

Figure 3:
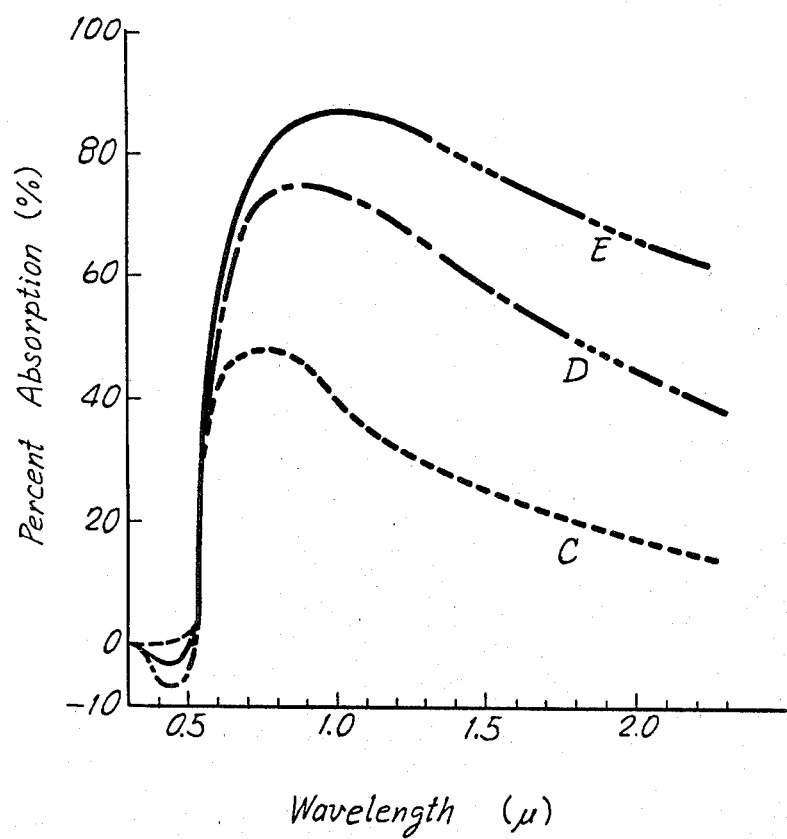
FIG. 3 is a graph which shows the change of percent absorption with reaction time of an antigen-antibody reaction.

FIG. 3 shows the relationship between the change in percent absorption of an antigen-antibody reaction mixture in the ordinate and the wavelength of light in microns in the abscissa at various reaction time when the antigen-antibody reaction is carried out in exactly the same manner as in Example 1 except that a polystyrene latex with an average particle diameter of 0.234 micron is used. In FIG. 3, Curves C, D and E denote the percent absorption of the reaction mixture after the antigen-antibody reaction is carried out for 3, 10 and 20 minutes, respectively.

As can be seen from FIG. 3, when the percent absorption of the antigen-antibody reaction mixture is determined with a light of a wavelength less than 0.6 micron, in the wavelength region of about 0.6 to 0.4 micron the progress of the reaction (i.e., the reaction time) does not correspond to the percent absorption, and in the wavelength region of not greater than about 0.4 micron the absorbance does not appreciably vary with the progress of the reaction. On the other hand, with a light of a wavelength of at least about 0.75 micron, the percent absorption of the reaction mixture gives a significantly good correlation to the reaction time or progress of the reaction. The dotted line sections in Curves C, D and E in FIG. 3 indicate that in these wavelength regions the percent absorption cannot be determined accurately even with an increased slit width, since the absorption by water is much higher in these regions.

As can be seen hereinafter from Example 4, when a polystyrene latex having an average particle diameter of 0.804 micron is used, a good correlation is established between the percent absorption of the antigen-antibody reaction mixture and the concentration of the antigen by the use of light of a wavelength longer than the average diameter by a factor of at least about 1.1, e.g., a wavelength of about 1.2 microns, as long as the concentration of the antigen in a sample is not greater than 0.6 μg/ml ($0.6 \times 10^{-6}$ g/ml). In this case, therefore, the quantitative determination according to this invention can be performed by irradiation with light having a wavelength of 1.2 microns or longer. In the case of those latex particles having a relatively small average diameter, however, as can be seen from FIG. 3, it is advantageous to use a near infrared light having a wavelength in the range of about 0.8 to 1.4 microns, preferably 1 to 1.4 microns and longer than the average diameter of the carrier by a factor of at least 2.

In accordance with one embodiment of this invention, it is desirable to irradiate a reaction mixture resulting from a carrier of a specific particle size on which an antibody or antigen is supported and an antigen or antibody or a mixture thereof in a sample solution with light of an appropriate wavelength in the range of 0.6 to 2.4 microns in order to preliminarily detect a wavelength region of applied light in which a quantitative correlation is established between the concentration of the particular antigen or antibody or a mixture thereof (including the reaction product) in the sample solution and the absorbance or percent absorption of the reaction mixture, and subsequently to effect the measurement of absorbance or percent absorption with light of a specific wavelength in this region.

Thus, in accordance with the invention, it is possible to determine the amount or concentration of an antigen and/or an antibody in a sample by using insoluble carrier particles having an average diameter of not greater than 1.6 microns, preferably in the range of 0.1 to 1.0 micron, more preferably 0.2 to 0.8 micron and most preferably in the range of 0.3 to 0.6 micron, supporting an antibody or an antigen on the carrier (i.e., sensitizing the carrier with the antibody or antigen), reacting the sensitized carrier with the antigen and/or antibody in the sample, and measuring the absorbance or percent absorption of the reaction mixture with light of a wavelength in the range of 0.6 to 2.4 microns, preferably 0.6 to 1.4 microns, more preferably 0.8 to 1.4 microns and most preferably 1 to 1.4 microns. As previously mentioned, the light to be applied should have a wavelength longer than the average diameter of the insoluble carrier particles by a factor of at least 1.1, preferably at least 1.5, with the proviso that this invention excludes the case where the reaction mixture is irradiated with light having a wavelength longer than the average diameter of the carrier particles by a factor of at least 1.5 to measure the absorbance of the reaction mixture.

The insoluble carrier particles useful for this invention include those organic polymer microparticles which are substantially insoluble in the particular liquid medium used for the measurement according to the invention and which have an average diameter within the above-mentioned range, such as, for example, latices of organic polymers such as polystyrene and styrene-butadiene copolymer obtained by emulsion polymerization; dispersed coccal bacteria such as staphylococci and streptococci, Bacillus prodigiosus, rickettsia, cell membrane fragments, etc.; as well as microparticles of inorganic oxides such as silica, silica-alumina and alumina, and finely pulverized minerals, metals and the like.

In accordance with the invention, an antibody or antigen which is reactive with the antigen and/or antibody in a sample to be determined is supported on the above-mentioned insoluble carrier particles such as, for example, latex particles (i.e., to sensitize the carrier). For this purpose, the antibody or antigen may be physically and/or chemically adsorbed on the carrier. Antibodies consist of proteins, whereas antigens are composed of one member selected from various substances such as, for example, proteins, polypeptides, steroids, polysaccharides, lipids, pollen, dust and the like.

There have already been proposed a number of methods for supporting these antibodies or antigens, particularly antibodies on insoluble carrier particles.

When an incomplete antigen, particularly a hapten is supported on insoluble carriers, it is advantageous to chemically modify the carriers with, for example, a coupling agent and subsequently adsorb the antigen chemically on the modified carriers.

If the carrier is a latex of a high molecular substance which has a functional group such as, e.g., sulfo, amino, or carboxyl or its reactive derivative group, an antigen and/or antibody can directly be adsorbed chemically on such latex.

As the liquid medium useful for this invention, water is the most preferably, although a mixture of water and a water-miscible organic solvent can be used. Suitable water-miscible organic solvents include alcohols such as methanol, ethanol, etc. and ketones such as acetone. Contrary to the known prior art methods which utilize the measurement of turbidity or the measurement of mean diffusion constant with a laser beam, the method according to this invention provides conditions that enable the insoluble carrier particles sensitized with an antibody or an antigen to react with a corresponding antigen and/or antibody as activity as possible.

On this account, in accordance with the invention, the insoluble carrier particles, for example, latex particles, which are sensitized with an antibody or an antigen (hereinafter referred to as "sensitized carrier particles") may be used as a suspension having a concentration of not less than 0.05% by weight, preferably in the range of 0.05 to 1%, more preferably 0.2 to 0.6%.

When the concentration of the sensitized carrier particles is much too high, as is apparent from FIG. 2, the transmittance of the suspension itself is so decreased that the measurement of absorbance or percent absorption according to the invention is made difficult. However, in the concentration range in which such a measurement of absorbance or percent absorption is possible, higher concentration of the sensitized carrier particles in the suspension is preferred, whereby it is possible to increase the sensitivity of the quantitative determination of antigens and antibodies.

In accordance with the invention, also contrary to the prior art methods, the sensitized carrier particles and and antigen- and/or antibody-containing sample are reacted under non-standing conditions.

For this purpose, the reaction may be advantageously carrier out under agitation. Since the reaction is generally carried out in a thin cell, the agitation is conveniently effected for example, by moving a rod vertically or transversely in the cell. Of course, the sensitized carrier particles and the sample may be reacted outside the cell for a certain period of time under predetermined conditions and thereafter the reaction mixture is placed in the cell for the measurement of absorbance or percent absorption. However, in order to make the reaction conditions reproducible, particularly with respect to reaction time in every measurement, the sensitized carrier particles and the sample may be reacted under predetermined non-standing conditions directly in a cell which has been set in a spectrophotometer, whereby more accurate determination can be achieved by measuring the absorbance or percent absorption.

Immediately after a prescribed period of reaction time or by measuring the time required to reach a predetermined value of absorbance or percent absorption while the reaction is continued under substantially fixed conditions.

In this way, the present invention not only makes it possible to determine such a concentration of an antigen and/or antibody in a sample that could heretofore be obserbed visually in a semiquantitative manner, but enables the determination of an antigen and/or antibody in such a trace amount that could heretofore be determined only by radioimmunoassay (RIA), with a precision equivalent to or higher than that of the RIA method.

In order to determine an antigen and/or antibody in a sample containing an unknown amount of the antigen and/or antibody in accordance with the invention, a set of dilute standard samples are prepared from a standard sample containing a definite amount of the same antigen and/or antibody by diluting it by various factors. Each of the dilute and undiluted standard samples is reacted under predetermined conditions with insoluble carrier particles sensitized with a definite amount of the corresponding antibody or antigen in accordance with the invention, and the absorbance or percent absorption of each reaction mixture is determined to prepare a standard curve for the particular combination of the antigen and/or antibody with the sensitized carrier particles, which indicates the relationship between the amount (concentration) of the antigen or antibody in the standard sample and the absorbance or percent absorption (this type of standard curve being hereinafter referred to as "Standard Curve A" for convenience). Subsequently, an unknown sample to be tested is reacted with the same sensitized carrier particles as that used in the preparation of the standard curve under substantially the same conditions as in the preparation of the standard curve, and the absorbance or percent absorption of the reaction mixture is measured.

The amount (or concentration) of the antigen and/or antibody in the unknown sample can be determined by comparing the value of absorbance or percent absorption thus obtained with Standard Curve A.

Alternatively, in the preparation of a standard curve like that described in the above, another type of standard curve which indicates the relationship between the amount (or concentration) of the antigen or antibody in the standard sample and the reaction time required to reach a predetermined value of absorbance or percent absorption may be prepared (this type of standard curve being hereinafter referred to as "Standard Curve B" for convenience). Also in this case, an unknown sample is reacted with the same sensitized carrier particles under substantially the same conditions as in the preparation of the standard curve, and the amount (or concentration) of the antigen and/or antibody in the unknown sample can be determined by reading the time required to reach the predetermined value of absorbance or percent absorption.

Thus, in accordance with the invention, the amount or concentration of an antigen and/or an antibody in an unknown sample may be determined by way of, either (A) the measurement of absorbance or percent absorption of the unknown sample (using Standard Curve A for calibration), or (B) the measurement of the rate of reaction, or the reaction time required for the absorbance or percent absorption to reach a certain value (using Standard Curve B for calibration).

As described previously, the above method (A) is useful as a determined system with a significantly high precision, not only when the concentration of an antigen and/or antibody in an unknown sample is relatively high, but even if it is so low that it could heretofore be determined only by the RIA method. On the other hand, the above method (B) wherein the reaction rate is measured is suitable for determining a relatively large amount (concentration) of an antigen and/or antibody in an unknown sample, but it is advantageous in that the measurement is quite simple.

According to our investigation, Standard Curve A as described above gives generally a gentle S-shaped curve rather than a straight line, but no unfavorable effect is found on the precision of the determination.

The reason why the curve assumes the S-shape as described above is presumed by us to be that the rate of reaction takes part in this shape at low concentrations of the antigen and/or antibody, whereas the saturation of active sites in the carrier takes part at higher concentrations.

It is possible, of course, to enlarge the linear portion in the S-shape curve by the selecting the conditions appropriately in the preparation of the standard curve, and apply substantially only this portion to the determination of unknown samples.

As stated above, the present invention is characterized in that the sensitized carrier particles at as high a concentration as possible are contacted and reacted with a sample.

Therefore, the cell for use in measuring the absorbance or percent absorption of the reaction mixture should have a thickness less than that of a cell for use in visible spectroscopic analysis, and, for example, those cells having thickness in the range of 0.5 to 10 mm, particularly 1 to 5 mm are preferred.

In order to effect a highly sensitive determination of a trace amount of an antigen or antibody which has heretofore been subjected to the RIA method, it is particularly advantageous:

(a) to use an antigen or antibody having as high an equilibrium constant as possible, (b) to use latex particles, particularly with an average diameter of 0.2 to 0.8 micron, the size distribution of which should be as narrow as possible, (c) to measure the absorbance or percent absorption with light of a wavelength of 1.0 to 1.4 microns (d) to select a relatively long reaction time, for example, in the range of 1 to 3 hours, and (e) to increase the concentration of the sensitized latex carrier as long as the absorbance or percent absorption is measurable at the concentration.

Also, in order to determine an unknown sample accurately in a relatively short time by the measurement of reaction rate (using Standard Curve B), it is advantageous, (f) to use latex particles having a relatively large average diameter, (g) to increase the concentration of the carrier particles in the latex as long as the measurement of absorbance or percent absorption is possible at the concentration, and (h) to use a relatively short period of reaction time, for example, in the range of 5 seconds to 10 minutes, preferably 10 seconds to 3 minutes.

In this case, when the time required for the absorbance or percent absorption to reach a predetermined value is plotted as the ordinate and the concentration as the abscissa, both on a log scale, the resulting Standard Curve B will give a straight line to advantage.

The present invention is described in the above with respect to the determination of an antigen and/or antibody in a sample by applying the latex agglutination phenomenon caused by contacting the antigen and/or antibody in the sample with sensitized carrier particles (i.e., LA system).

The method according to the invention is also suitable for the determination of a sample using its inhibitory action against the above-mentioned agglutination reaction (i.e., LI system).

Incomplete antigen such as, for example, haptens can be determined by applying the method according to the invention to the LI system.

In this case, for instance, an antigen may be supported on the insoluble carrier particles used in this invention, the sensitized carrier particles are reacted competitively with a given amount of an antibody which has been reacted with an antigen of a known concentration (i.e., a standard antigen solution), and the absorbance or percent absorption of the resulting reaction mixture is measured. The above procedure is repeated at various concentrations of the standard antigen solutions to prepare Standard Curve C. Subsequently, an unknown sample is reacted with the same antibody of the definite concentration, and the resulting reaction mixture is the reacted with the sensitized carrier. These reactions should be carried out under substantially the same conditions as in the preparation of Standard Curve C. The absorbance or percent absorption of the final reaction mixture with the sensitized carrier particles is measured and compared with the standard curve (C) to determine the amount (concentration) of the antigen in the unknown sample.

Following the procedure of the above-mentioned LI system except that a certain antibody is supported on the insoluble carrier particles, an antibody in an unknown sample can be determined by the LI system. In addition, it is possible, if desired, to support both an antigen and an antibody of different species on the insoluble carrier particles and determine an antigen and an antibody in an unknown sample.

Thus, in accordance with the invention, the quantitative determination of a wide variety of antigens and/or antibodies are possible, for example, (1) blood examination of subjects or blood donors which is indispensable for emergency operations, for example, detection of blood group substances, the Au- or HB-antigen or other contaminants in the blood, or determination of fibrin/fibrinogen degradation products (FDP) which is recently regarded as useful in the convalescent control for kidney transplantation or renal failure patients, (2) determination of human chorionic gonadotropin (hCG) which is regarded as significantly important in the pregnancy diagnosis or the convalescent control of chorioepithelioma, (3) determination of hCG, or urinary estriol glucuronide which is a metabolite of follicular hormone, said determination being required for monitoring pregnancy, (4) determination of oxytocin in blood which is considered to be a uterine contraction inducer, (5) determination of certain adrenal cortical hormones such as corticoids and aldosterone, or adrenocorticotropic hormones (ACTH), (6) determination of insulin for diabetics, or determination of follicle stimulating hormone, luteinizing hormone, estrogens, corpus luteum hormone, etc., (7) determination of gastrin or secretin which is a gastrointestinal hormone, (8) detection and determination of an antibody in the body fluid of patients with allergy, syphilis, or hemolytic streptococcicosis, rubella, antoimmune diseases such as collagen disease and other infection diseases, and the like.

The present invention may be adopted, of course, for the qualitative or semi-quantitative measurement of these antigens and/or antibodies.

In accordance with another aspect of this invention, there is provided a novel apparatus for measuring antigens and antibodies which can be used in the above-mentioned method of this invention.

The apparatus according to the invention involves (a) insoluble carrier particles for supporting an antibody or antigen, said carrier particles having an average diameter of not greater than 1.6 microns, (b) an absorption cell for holding a reaction mixture obtained by reacting the antibody or antigen supported on the insoluble carrier and a corresponding antigen and/or antibody in a liquid medium, said cell having a thickness in the range of 0.5 to 10 mm, (c) a photometer for the measurement of absorbance or percent absorption equipped with an irradiation unit capable of applying light of a particular wavelength in the range of 0.6 to 2.4 microns.

The measuring apparatus according to this invention may possess the same basic structure as in the prior art photometric apparatus, except for the essential structural characteristics as described in (a), (b) and (c).

Figure 4:
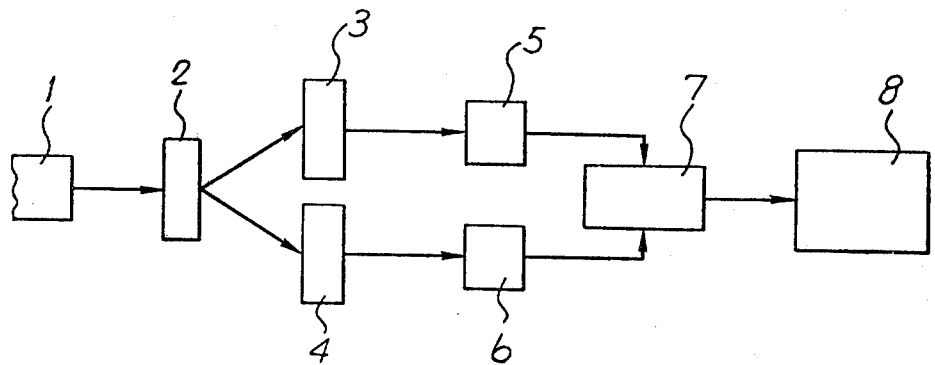
FIG. 4 is a systematic diagram which illustrates the basic structure of the apparatus for use in the invention.

Thus, as illustrated in FIG. 4, the basic structure of the apparatus according to the invention comprises an irradiation unit comprising light source (1) and filter or prism (2); sample cell (3) for holding a sample of an antigen-antibody reaction mixture to be measured, and reference cell (4) for holding a control sample for compensation; photocells (5) and (6) for sensing the intensities of light transmitted by the respective cells and transforming them into electric signals; amplifier (7) for amplifying the electric signals; and displaying or recording unit (8) for displaying or recording the amplified electric signals.

Light source (1) may be a conventional tungsten lamp and the light emitted from light source (1) is monochromatized through filter or prism (2) so as to apply a light beam of a specific wavelength in the range of 0.6 to 2.4 microns, preferably 0.8 to 1.8 microns and more preferably 0.9 to 1.4 microns to cells (4) and (5).

Filter or prism (2) is therefore selected from those capable of effectively monochromatizing the light of the abovementioned wavelengths. For instance, an interference filter of 1,200±50 millimicrons may be used as the filter or a quartz or glass prism as the prism.

The applying light thus monochromatized is converged appropriately through a slit or a lens before it is applied to sample cell (3) and reference cell (4).

Figure 5:
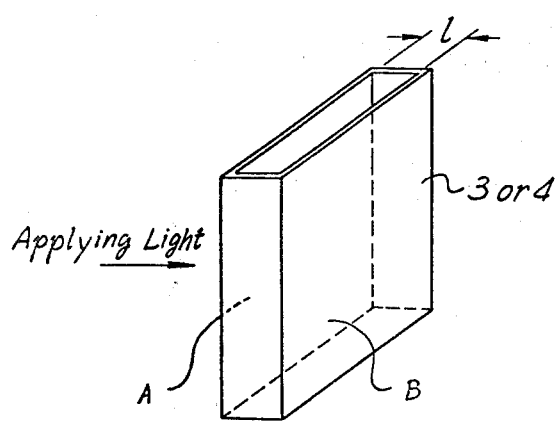
FIG. 5 is a perspective view of an absorption cell useful for both samples and controls.

Sample cell (3) and reference cell (4) may be composed of transparent glass or synthetic resin (e.g., acrylic resins) and may generally be a box-shape having a rectangular cross section (See FIG. 5). The cell thickness, that is, the distance (l) between windows (transmissive windows) (a) and (b), respectively, on the side from which the light is applied and on the opposite side, may be in the range of 0.5 to 10 mm, preferably 1 to 5 mm. The transmissive windows may advantageously possess at least 30% transmission, preferably 80% or higher transmission, for lights of wavelengths of 0.6 to 2.4 microns.

In sample cell (3) is placed a reaction mixture prepared by reacting an antigen or antibody or a mixture thereof with the corresponding antibody and/or antigen supported on insoluble carrier particles in a liquid medium in such a manner as previously described with respect to the method of this invention. On the other hand, in reference cell (4) is placed a control sample prepared by dispersing only the antibody- and/or antigen-sensitized insoluble carrier particles in the liquid medium.

The light beams transmitted by cells (3) and (4), are received by photocells (5) and (6), respectively, and transformed into electric signals, the respective amplitudes of which are in proportion to the respective intensities of light received by the cells. As photocells (5) and (6), any type of photocells which function to transduce an intensity of light received into an electric signal having a strength proportional to the intensity of light may be used. Lead sulfide photoconductive element, for example, may be employed to advantage.

The electric signals thus transformed by the photocells may be amplified by amplifier (7) in a conventional manner and displayed or recorded on indicator or recorder (8) so as to read them visually.

If a horological mechanism is incorporated in indicator or recorder (8), it is possible to automatically record the absorbance or percent absorption after a predetermined period of reaction time, or record the time required for the absorbance or percent absorption to reach a predetermined value.

In preferred embodiment of the apparatus according to the invention, sample cell (3) is equipped with an agitator, which may be a mixed rod movable in the cell.

Figure 6:
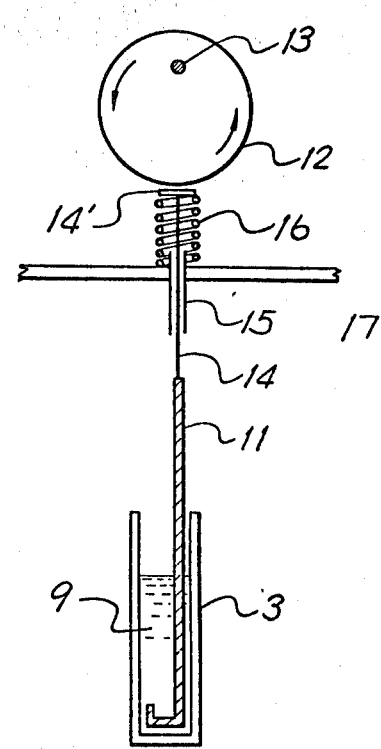
FIG. 6 is a schematic diagram of a stirring mechanism which may preferably be used in the practice of this invention.

FIG. 6 shows a preferred embodiment of the agitator mechanism for agitating mixture 9 of a sample and sensitized carrier particles (e.g., sensitized latex) which is held in sample cell 3 used in the apparatus of the invention.

Referring to FIG. 6, L-shaped mixing rod 11 can move up and down to agitate mixture 9 in cell 3 by the vertical up and down motion of T-shaped hammer-headed connecting rod 14, said connecting rod 14 being contacted at its upper flat plate 14' with rotary disc 12 which is driven by eccentric shaft 13. FIG. 17 indicates a light-shielding lid, and connecting rod 14 moves up and down through hollow tube 15 fixed to and through lid 17, wherein connecting rod 14 goes down with rotation of eccentric disc 12 and is then lifted by the restoring force of spring 16 which is provided between lid 17 and upper flat plate 14' of connecting rod 14.

When sample cell 3 to be used in the photometric apparatus as shown in FIG. 4 has such a structure, for example, as shown in FIG. 6, cell 3 can be placed in the dark which is shielded from sunlight and a mixture of a sample and sensitized carrier particles (sensitized latex) introduced in cell 3 can be mixed with L-shaped mixing rod 11 while being irradiated with near infrared light of a predetermined wavelength, whereby it is possible to agitate the mixture without obstruction to the light path of the near infrared light.

Thus, by the use of the above-mentioned apparatus, the antigen-antibody reaction between the sample and the sensitized carrier particles can be accelerated while being progressed under substantially fixed conditions, and in addition, such operation as to stop the reaction immediately after a predetermined period of reaction time has passed or to accurately read the reaction time elapsed by the time the absorbance or percent absorption reaches a predetermined value can be extremely readily performed.

Having generally described this invention, a more complete understanding can be obtained by reference to certain examples which are provided herein for purpose of illustration only and are not intended to be limiting in any manner.

EXAMPLE 1

(1) Preparation of an antifibrinogen antibody-sensitized latex (anti-Fg-latex) reagent To 10 ml of a glycine buffer solution of anti-(human fibrinogen (Fg)) antibody (2 mg/ml concentration), 1 ml of a polystyrene latex with an average particle diameter of 0.481 micron (Dow Chemical Co., 10% solids content by weight) is added, and the mixture is stirred at room temperature for 30 minutes, then warmed to 40° C. and stirred for an additional 30 minutes at this temperature; and centrifuged (at 12,000 rpm) for 50 minutes with cooling at 2° to 4° C.

The precipitates are separated by decantation and the collected anti-Fg antibody-sensitized latex particles are suspended in a bovine serum albumin solution (0.2 wt. % concentration) to prepare an anti-Fg-sensitized latex reagent containing the sensitized latex particles at a concentration of 1% by weight.

(2) Preparation of a standard curve

A 0.1 ml aliquot of the anti-Fg-latex reagent as prepared in Part (1) is placed in a plastic test tube (7 mm inner diameter×70 mm long) together with 0.3 ml of a standard fibrinogen (Fg) solution (in an isotonic sodium chloride solution containing 0.2% by weight bovine serum albumin) which contains Fg at a concentration indicated in Table-A below, and the mixture is shaken at room temperature for 20 minutes on a reciprocal shaker at 200 strokes per minute to effect the antigen-antibody reaction. Immediately thereafter, the reaction mixture in the test tube is transferred to a glass absorption cell having a thickness of 2 mm and the percent absorption of the reaction mixture is measured at a wavelength of the applied light of 1.2 microns with an automatic recording spectrophotometer (Hitachi Ltd., Model EPS-3; using as a control a suspension of 0.1 ml of the anti-Fg-latex reagent diluted with 0.3 ml of the isotonic sodium chloride solution containing 0.2% by weight bovine serum albumin). The measurements are taken twice with each standard Fg solution. The results are summarized in the following Table A.

Table-A

| Concentration of standard Fg solution ($\mu$g/ml) | % Absorption at 1.2 $\mu$ | | |
|---|---|---|---|
| | First | Second | Mean |
| 0.1 | 53.9 | 56.6 | 55.3 |
| 0.2 | 85.4 | 83.4 | 84.4 |
| 0.3 | 91.7 | 93.2 | 92.5 |
| 0.4 | 95.3 | 95.3 | 95.3 |
| 0.5 | 96 | 96.3 | 96.2 |

Figure 7:
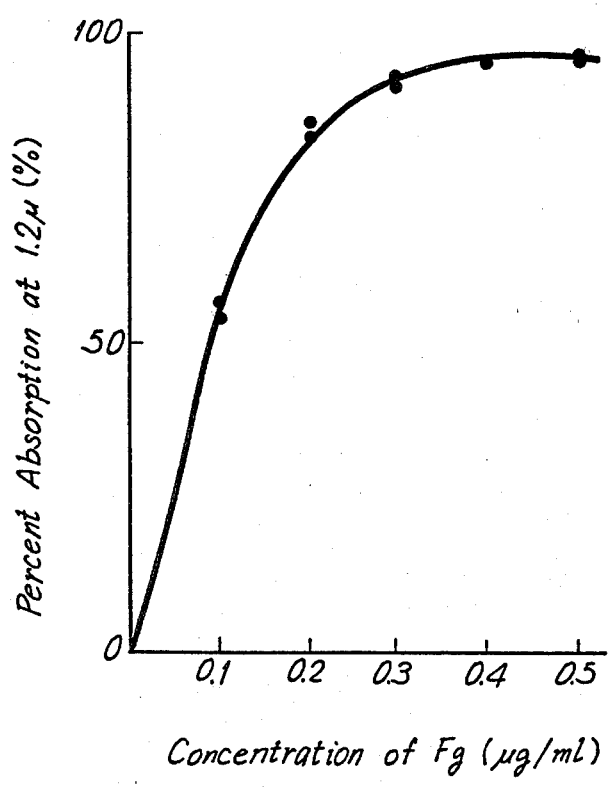
FIG. 7 shows a standard curve of percent absorption at a wavelength of 1.2 microns using standard Fg solutions and anti-Fg-polystyrene latex particles with an average diameter of 0.481 micron.

When the above data are plotted graphically with concentration of standard Fg solution as abscissa and percent absorption (mean value) at 1.2 microns (in wavelength of the applied light) as ordinate, a standard curve as shown in FIG. 7 is obtained.

(3) Quantitative determination of Fg in unknown samples

A sample of blood, urine or fluid in the thoracic cavity (intrapleural fluid) is collected from a subject and if the sample is blood, the serum or plasma is separated therefrom. A 0.3 ml aliquot of the sample or its diluted sample is treated with 0.1 ml of the anti-Fg-latex reagent as prepared in Part (1) in exactly the same manner as described in Part (2), and the percent absorption is measured in the same manner as described in Part (2). Using the standard curve obtained in Part (2), the concentration of Fg corresponding to the value of percent absorption is read and the results are summarized in Table-B below.

For the purpose of comparison, Table-B also involves the data obtained in accordance with the conventional radioimmunoassay (RIA) method (S. M. Ratkey, et al., Brit. J. Haematol. 30, 145–149, 1975) and slide method (Fujimaki, Tamura and Takahashi, Rinsho Kagaku (Clinical Science), Vol. 12, 507, 1976; and Fujimaki, Ikematsu, Takeuchi and Kato, Rinsho Byori (Japanese Journal of Clinical Pathology), 21, 973, 1973).

Table-B

| Subject No. | Unknown sample Material | Dilution factor | % Absorption measured | Fg concentration in unknown sample ($\mu$g/ml) | | |
|---|---|---|---|---|---|---|
| | | | | Method of this invention | RIA method | Slide method |
| 1 | Urine | × 2 | 82.7 | 0.402 | 0.359 | 0.5 |
| 2 | " | × 16 | 93.1 | 5.178 | 5.117 | 8.0 |
| 3 | " | × 1 | 94.1 | 0.347 | 0.368 | 0.5 |
| 4 | " | " | 18.7 | 0.021 | 0.024 | less than 0.5 |
| 5 | " | " | 2.5 | 0.003 | 0.006 | less than 0.5 |
| 6 | " | " | 33.1 | 0.042 | 0.037 | less than 0.5 |
| 7 | " | " | 13.0 | 0.016 | 0.011 | less than 0.5 |
| 8 | " | " | 32.5 | 0.041 | 0.008 | less than 0.5 |
| 9 | " | " | 4.5 | 0.005 | 0.007 | less than 0.5 |
| 10 | " | " | 36.8 | 0.048 | 0.072 | less than 0.5 |
| 11 | Serum | × 10 | 51.0 | 0.760 | 0.800 | 1.0 |
| 12 | " | " | 53.2 | 0.812 | 0.863 | 0.9 |
| 13 | " | " | 69.8 | 1.317 | 1.335 | 1.25 |
| 14 | " | " | 55.1 | 0.858 | 0.892 | 1.0 |
| 15 | Fg-free Plasma | " | 71.8 | 1.400 | 1.520 | 2.0 |
| 16 | Cancerous intrapleural fluid | × 640 | 93.8 | 217.12 | 197.4 | 320 |

From the above results, it can been seen that the data of Fg concentration obtained by the method of this invention are in significantly close agreement with those obtained by the RIA method which is known as the most precise determination method of the conventional methods. The correlation coefficient between the method of this invention and the RIA method is 0.999 or higher.

EXAMPLE 2

An anti-Fg-sensitized latex reagent (containing 1% by weight latex particles) is prepared in the same manner as in Example 1, Part (1), except for use of another polystyrene latex having an average particle diameter of 0.234 micron (Dow Chemical Co., 10% solids content by weight). A 0.1 ml aliquot of the anti-Fg-sensitized latex reagent thus obtained is mixed with 0.3 ml of a standard Fg solution (containing 0.5 $\mu$g/ml of Fg) and shaken at room temperature for 5 minutes on a reciprocal shaker at 250 strokes per minute to carry out the antigen-antibody reaction. Subsequently, the percent absorption of the reaction mixture is measured at a wavelength of applied light of 1.2 microns in the same manner as described in Example 1, Part (2). In order to confirm the reproducibility of the measurement, the same procedure is repeated three more times. The results are given in Table-C below.

Following the above-mentioned measuring test except for use of the serum isolated from a blood sample collected from a patient instead of the standard Fg solution, the same procedure as described above is repeated four times on different days to confirm the reproducibility of the measurement for the actual body fluid. The results are also given in the following Table-C.

Table-C

| Measurement No. | % Absorption | |
|---|---|---|
| | Standard Fg solution | Serum |
| 1 | 73.8 | 49.1 |
| 2 | 72.8 | 47.5 |
| 3 | 72.6 | 50.5 |
| 4 | 71.5 | 48.3 |
| Average | 72.9 ± 1.3 | 49.05 ± 1.55 |
| Coefficient of variance | 1.8% | 3.4% |

As is apparent from the results given in Table-C above, the method of this invention possesses an excellent reproducibility both in the case of using the standard Fg solution sample and in the case of using the actual body fluid (serum) sample.

EXAMPLE 3

To 5 ml of a glycine buffer solution, 100 mg of silica microparticles (prepared in the same manner as described in Example 1 of Japanese Patent Laying-Open Publication No. 120497/75) having an average diameter of 0.32 micron (although containing 15% of those particles having diameters of 0.5 micron or greater) are added and the mixture is subjected to ultrasonic vibrations of 28 KHz for an hour to form a suspension of silica microparticles. An anti-Fg-antibody-sensitized silica suspension reagent is prepared in the same manner as described in Example 1, Part (1) except for use of the silica microparticle-containing suspension thus prepared instead of the polystyrene latex with an average diameter of 0.481 micron in Example 1, Part (1) and use of another concentration of bovine serum albumin solution (0.05% concentration by weight).

Using the anti-Fg-sensitized silica suspension reagent, the percent absorption is measured with each standard Fg solution in the same manner as described in Example 1, Part (2). The results are summarized in the following Table-D.

Table-D

| Concentration of standard Fg solution (μg/ml) | % Absorption at 1.2 μ |
|---|---|
| 0.2 | 6.2 |
| 0.4 | 25.1 |
| 0.6 | 48.3 |
| 0.8 | 65.3 |
| 1.0 | 76.7 |

Figure 8:
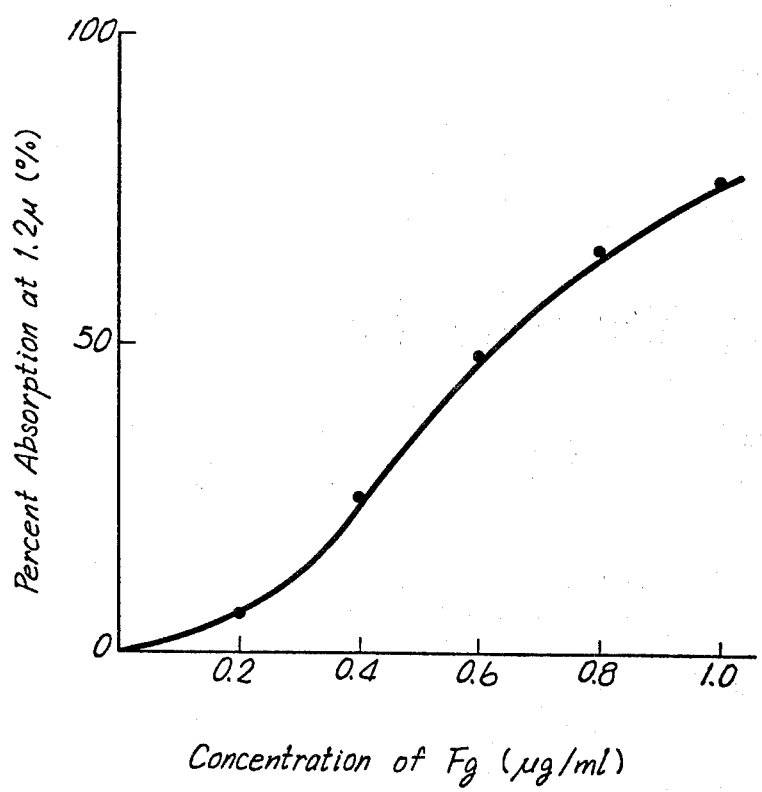
FIG. 8 shows a standard curve of percent absorption measured at a wavelength of 1.2 microns using an anti-Fg-silica particles with an average diameter of 0.32 micron and a set of standard Fe solutions.

A standard curve is plotted from the above data as in Example 1, Part (2), said standard curve being shown in FIG. 8. It can be seen from FIG. 8 that a clean linear relationship is established between the concentration of Fg and the percent absorption when the concentration of standard Fg solution is higher than 0.4 μg/ml. Unknown samples (urine, serum and intrapleural fluid) collected from subjects are subjected to the same procedure as described in Example 1, Part (3) to determine Fg in the unknown samples using the above standard curve. The results are summarized in the following Table-E.

Table-E

| Subject No. | Unknown sample Material | Dilution factor | % Absorption measured | Fg concentration in unknown sample (μg/ml) Method of this invention | RIA method |
|---|---|---|---|---|---|
| 1 | Urine | × 1 | 25.0 | 0.400 | 0.359 |
| 2 | " | × 10 | 38.3 | 5.000 | 5.117 |
| 3 | " | × 1 | 22.4 | 0.380 | 0.368 |
| 4 | Serum | × 1 | 63.7 | 0.770 | 0.800 |
| 5 | " | × 1 | 67.6 | 0.830 | 0.892 |
| 6 | Cancerous intrapleural fluid | × 400 | 38.4 | 200 | 197.4 |

EXAMPLE 4

The percent absorption is measured at wavelengths of applied light of 1.2 and 1.7 microns in the same manner as desdribed in Example 1, Parts (1) and (2), except for use of a polystyrene latex with an average particle diameter of 0.804 micron (Dow Chemical Co., 10% solids content by weight) instead of the polystyrene latex with an average diameter of 0.481 micron (Dow Chemical Co.) and of another concentration of bovine serum albumin (0.1% concentration by weight). The results are given in the following Table-F.

Table-F

| Concentration of standard Fg solution (μg/ml) | % Absorption at | |
|---|---|---|
| | 1.2 μ | 1.7 μ |
| 0.2 | 25.4 | 17.4 |
| 0.4 | 44.7 | 38.1 |
| 0.6 | 61.9 | 64.7 |
| 0.8 | 59.1 | 74.4 |
| 1.0 | 44.7 | 76.1 |

From the results shown in Table-F, it can be seen that a clear correlation is established between the concentration of Fg and the percent absorption when the wavelength of the applied light is longer than the average diameter of the solid carrier particles (polystyrene latex particles) by a factor exceeding 2.

EXAMPLE 5

Following the procedure as described in Example 1, Part (1), except that the anti-human fibrinogen antibody is replaced by anti-(human chorionic gonadotropin antibody (anti-hCG)) and the polystyrene latex with an average diameter of 0.481 micron by another polystyrene latex with an average particle diameter of 0.234 micron (Dow Chemical Co.), an anti-hCG-sensitized latex reagent is prepared. Using the anti-hCG-sensitized latex reagent thus obtained, the percent absorption is measured at a wavelength of the applied light of 1.2 microns in the same manner as described in Example 1, Part (2), except for use of standard hCG solutions instead of the standard Fg solutions. The results are summarized in the following Table-G.

Table-G

| Concentration of standard hCG solution (IU/ml) | % Absorption at 1.2 microns |
|---|---|
| 0.1 | 10.5 |
| 0.2 | 25.9 |
| 0.3 | 32.1 |
| 0.4 | 45.2 |

Table-G-continued

| Concentration of standard hCG solution (IU/ml) | % Absorption at 1.2 microns |
| --- | --- |
| 0.5 | 56.3 |
| 0.7 | 76.6 |
| 1.0 | 89.3 |

A standard curve is prepared from the above data in the same manner as described above. On the other hand, urine samples are collected from several subjects and subjected to the determination of urinary hCG in the same manner as described in Example 1, Part (3). The results are summarized in the following Table-H.

Table-H

| Subject No. | Unknown samples Material | Dilution factor | % Absorption measured | hCG concentration in unknown sample (IU/ml) Method of this invention | RIA Method |
| --- | --- | --- | --- | --- | --- |
| 1 | Urine | × 1 | 60.2 | 0.564 | 0.482 |
| 2 | " | " | 92.4 | 0.966 | 1.120 |
| 3 | " | " | 88.9 | 0.944 | 0.857 |
| 4 | " | " | 89.8 | 0.952 | 0.925 |

EXAMPLE 6

In a glass absorption cell having a thickness of 2 mm equipped with an L-shaped stirring rod, 0.1 ml of the anti-Fg-sensitized latex reagent as prepared in Example 2 and 0.3 ml of one of standard Fg solutions having concentrations of Fg as indicated in Table-I below are placed, and the percent absorption of the reaction mixture is monitored continuously at a wavelength of the applied light of 1.2 microns in the same manner as described in Example 1, Part (2) in order to read the time required to each 68.4% absorption while the stirring rod is moved up and down vertically at a definite speed of 200 vibrations per minute. The results are given in the following Table-I.

Table-I

| Concentration of standard Fg solution (mg/ml) | Time required to reach 68.4% absorption (sec.) |
| --- | --- |
| 2 | 26.9 |
| 4 | 11.3 |
| 6 | 6.4 |
| 8 | 4.7 |
| 10 | 2.9 |

Figure 9:
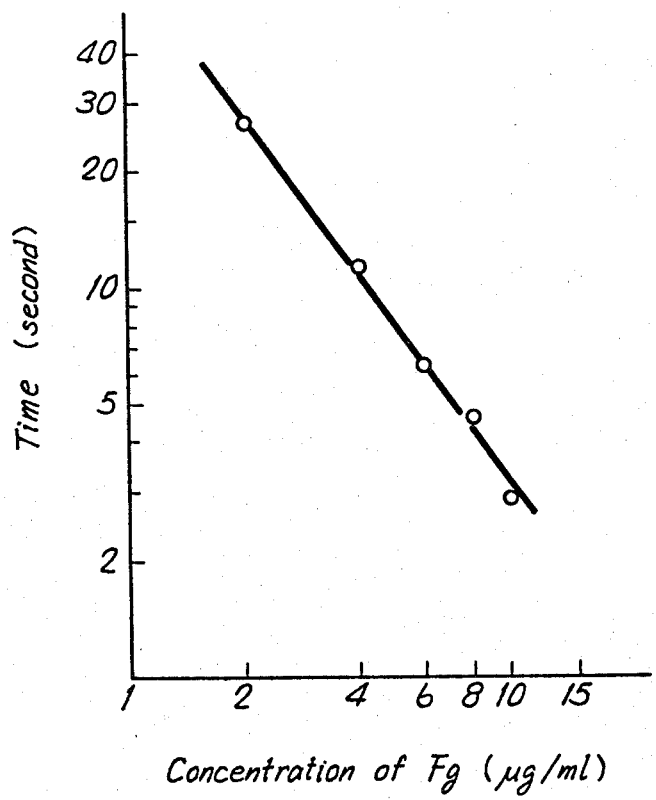
FIG. 9 shows a standard curve of time required to reach 68.4% absorption at a wavelength of 1.2 microns, when an anti-Fg-sensitized latex reagent is reacted with each of standard Fg solutions at various concentrations.

The above data are plotted on log-log graph paper with concentration of standard Fg solution as abscissa and time required to reach 68.4% absorption as ordinate so as to prepare a standard curve. The standard curve, as shown in FIG. 9, gives a clean straight line.

Then, 0.3 ml of an unknown sample (urine, serum or intrapleural fluid) collected from a subject and 0.1 ml of the above-mentioned anti-Fg-sensitized latex reagent are placed in a glass absorption cell having a thickness of 2 mm equipped with an L-shaped stirring rod and the time required to reach 68.4% absorption is measured at a wavelength of the applied light of 1.2 microns in the same manner as above, whereupon the value of Fg concentration corresponding to the length of time measured is read from the standard curve as prepared in the above. The results are summarized in the following Table-J.

Table-J

| Subject No. | Unknown sample Material | Dilution factor | Time required to reach 68.4% absorption (sec.) | Fg concentration in unknown sample (μg/ml) Method of this invention | RIA Method |
| --- | --- | --- | --- | --- | --- |
| 1 | Urine | × 1 | 9.2 | 4.5 | 5.117 |
| 2 | Cancerous intrapleural fluid | × 50 | 11 | 195 | 197.4 |
| 3 | Serum | × 1 | 25 | 2.1 | 2.210 |
| 4 | " | × 1 | 20 | 2.5 | 2.302 |
| 5 | " | × 1 | 3.8 | 8.6 | 9.020 |
| 6 | " | × 1 | 12 | 3.7 | 3.723 |

EXAMPLE 7

(1) Preparation of an oxytocin-sensitized latex reagent

One (1.0) ml of an oxytocin solution at a concentration of 220 IU/ml dissolved in aqueous 0.1 N acetic acid solution is mixed with 0.5 ml of a polystyrene latex with an average particle diameter of 0.481 micron (Dow Chemical Co., 10% solids content by weight), and the mixture is stirred at room temperature for 2 hours and then centrifuged (at 12,000 rpm) for 20 minutes under cooling at 2° to 4° C. The precipitates are separated by decantation and the collected oxytocin-sensitized latex particles are dispersed in 4 ml of an EDTA-glycine buffer solution containing 0.2% by weight bovine serum albumin so as to prepare an oxytocin-sensitized latex reagent which contains the latex particles at a concentration of 1% by weight.

(2) Decision of the optimum concentration of oxytocin antiserum

A 0.1 ml aliquot of the oxytocin-sensitized latex reagent as prepared in Part (1) is mixed with 0.1 ml of an isotonic sodium chloride solution and 0.2 ml of oxytocin antiserum which has been diluted with an isotonic sodium chloride solution by a factor indicated in Table-K below. The mixture is shaken on a reciprocal shaker at 200 strokes per minute for 12 minutes and the percent absorption is measured at a wavelength of the applied light of 1.2 microns in the same manner as described in Example 1, Part (2). The results are given in the following Table-K.

Table-K

| Dilution factor of oxytocin antiserum | Absorption at 1.2 μ |
| --- | --- |
| × 20 | 93.3 |
| × 30 | 75.9 |
| × 40 | 59.5 |
| × 50 | 52.8 |
| × 80 | 39.7 |
| × 100 | 31.1 |

From the above data, it is decided that the optimum concentration of the oxytocin antiserum resides in around a dilution factor of about 30.

(3) Preparation of a standard curve

In a plastic test tube, 0.2 ml of a solution prepared by diluting the oxytocin antiserum as used in Part (2) above by a factor of 30 and 0.1 ml of a standard oxytocin solution (dissolved in an aqueous 0.1 N acetic acid) at a concentration indicated in Table-L below are placed and thoroughly mixed. After the mixture is allowed to stand at room temperature for 30 minutes, 0.1 ml of the oxytocin-sensitized latex reagent as prepared in Part (1) above is added to the test tube and the resulting mixture is shaken on a reciprocal shaker at 200 strokes per minute for 12 minutes. The liquid thus obtained is placed in a glass absorption cell with a thickness of 2 mm and the percent absorption is measured at a wavelength of the applied light of 1.2 microns in the same manner as described in Example 1, Part (2). The results are summarized in the following Table-L.

Table-L

| Concentration of standard oxytocin solution (μIU/ml) | % Absorption at 1.2 μ | ΔD* |
|---|---|---|
| 2,000 | 59.8 | 13.8 |
| 1,500 | 64.5 | 9.1 |
| 1,000 | 67.1 | 6.5 |
| 500 | 70.2 | 3.8 |
| 300 | 71.8 | 1.8 |
| 0 | 73.6 | — |

*ΔD = (% absorption at zero concentration of the standard oxytocin solution) minus (% absorption at the indicated concentration of the same)

Figure 10:
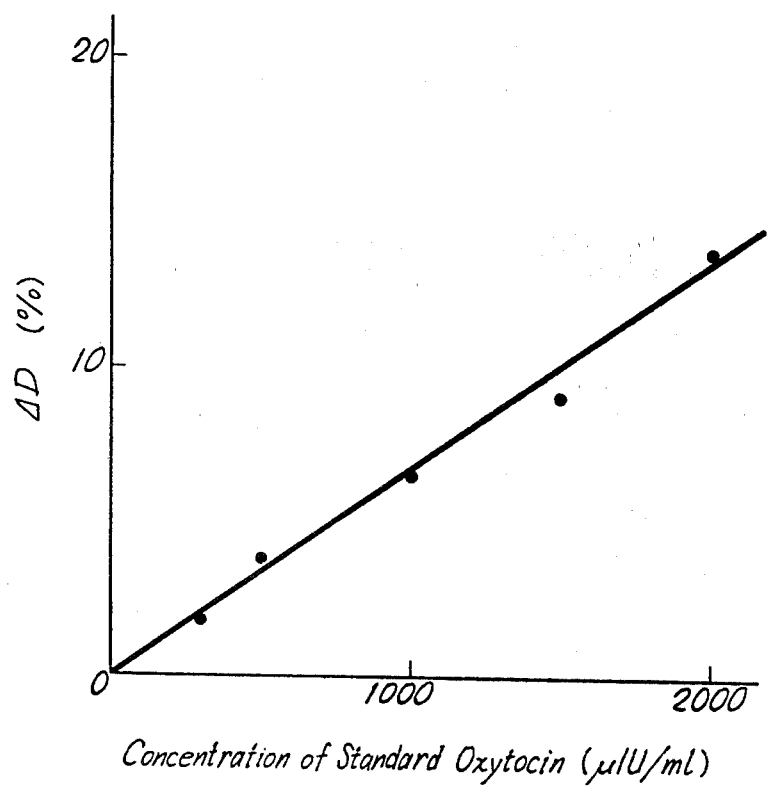
FIG. 10 shows a standard curve of percent absorption measured at a wavelength of 1.2 microns after oxytocin antiserum is reacted with each of standard oxytocin solutions at various concentrations and oxytocinsensitized latex particles are then added to the reaction mixture.

When the above data are plotted graphically with concentration of standard oxytocin solution as abscissa and ΔD as ordinate, a clean linear relationship is established as shown in FIG. 10.

Using the standard curve thus prepared, it is possible to effect the determination of oxytocin in the serum samples of pregnant women.

EXAMPLE 8

(1) Preparation of an hCG-sensitized latex reagent

In 5 ml of 0.05 N hydrochloric acid, 7,900 IU/ml of human chorionic gonadotropin (hCG) is dissolved and hydrolyzed at 80° C. for an hour. After the solution is subjected to dialysis and subsequent suction filtration, the hydrolyzed hCG thus obtained is dissolved in 2 ml of a 0.05 M borate buffer solution (pH 8.7) and diluted to 10 ml in the total volume.

A 5 ml aliquot of a 2% solution of a polystyrene latex (Dow Chemical Co., 10% solids content by weight) with an average particle diameter of 0.481 micron is gradually added to the hydrolyzed hCG solution under stirring. The resulting hCG-sensitized latex particles are centrifuged at 13,000 rpm for 20 minutes and the sensitized latex particles precipitated are separated and suspended in 10 ml of a 0.2% solution of bovine serum albumin in the borate buffer solution. The suspension is then centrifuged and the collected precipitates are centrifugally washed with the borate buffer solution and finally suspended in 10 ml of the buffer solution so as to provide an hCG-sensitized latex reagent containing 1% by weight latex particles.

(2) Preparation of a standard curve

The optimum concentration (i.e., dilution by a factor of 300 in this case) of anti-hCG serum is decided in the same manner as described in Example 7, Part (2). In a plastic test tube, 0.2 ml of an anti-hCG serum solution prepared by diluting the serum with an isotonic sodium chloride solution by a factor of 300 and 0.1 ml of a standard hCG solution at a concentration indicated in Table-M below are placed and shaken for 10 minutes. Subsequently 0.1 ml of the hCG-sensitized latex reagent as prepared in Part (1) above is added and the mixture is shaken for 10 minutes on a reciprocal shaker at 200 strokes per minute. The resulting liquid is placed in a glass absorption cell with a thickness of 2 mm and the percent absorption is measured at a wavelength of the applied light of 1.0 micron in the same manner as described in the foregoing Example 1, Part (2). The results are given in the following Table-M.

Table-M

| Concentration of standard hCG solution (IU/ml) | % Absorption at 1.0 μ |
|---|---|
| 10 | 27.6 |
| 1 | 37.0 |
| 0.1 | 46.4 |

Figure 11:
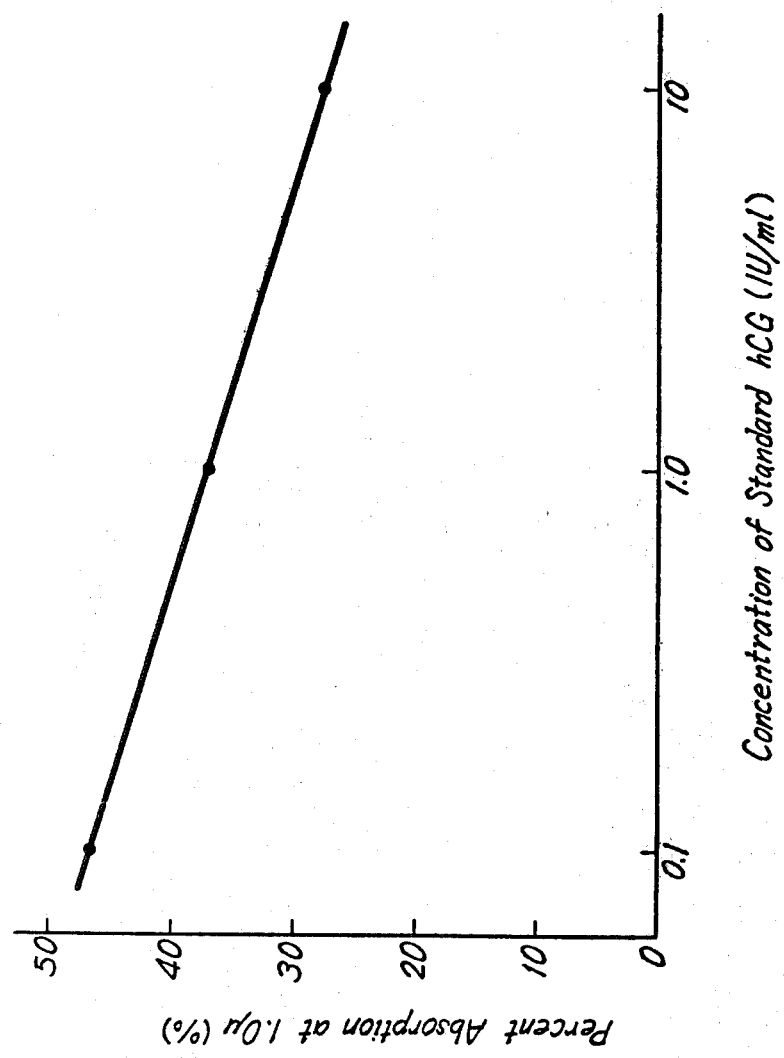
FIG. 11 shows a standard curve of percent absorption measured at 1.0 micron after anti-hCG serum is reacted with each of standard hCG solutions at various concentrations and hCG-sensitized latex particles are then added to the reaction mixture.

When the above data are plotted graphically with logarithm of concentration of standard hCG solution as abscissa and percent absorption as ordinate, the standard curve prepared gives a clean straight line, as shown in FIG. 11, in these concentrations at which the measurement is actually carried out. Thus, it is possible to effect the determination of hCG in the serum samples from patients of chorioepithelioma

EXAMPLE 9

In a plastic test tube, 0.1 ml of the anti-Fg-sensitized latex reagent as prepared in Example 1, Part (1) (the average diameter of the polystyrene latex particles: 0.481 micron; sensitized latex particles content: 1% by weight) and 0.3 ml of a standard Fg solution (dissolved in an isotonic sodium chloride solution containing 0.5% by weight bovine serum albumin) at a concentration indicated in Table-N below are mixed thoroughly and then shaken for 3 hours on a reciprocal shaker at 200 storkes per minute. Subsequently the percent absorption is measured at a wavelength of the applied light of 1.2 microns in the same manner as described in Example 1, Part (2). The results are shown in the following Table-N.

Table-N

| Concentration of standard Fg solution (ng/ml) | % Absorption at 1.2 μ |
|---|---|
| 10 | 11.5 |
| 20 | 25 |
| 40 | 52.6 |
| 60 | 71.2 |
| 80 | 80.8 |
| 100 | 84.3 |

When a standard curve is prepared on the basis of the above data, a clear correlation is found between the concentration of the standard Fg solution and the percent absorption. Thus, in accordance with the invention, it is possible to determine ultramicro amounts of Fg of the order of ng (nanograms)/ml, and such high sensitivity is comparable to that of the RIA method.

EXAMPLE 10

Figure 12:
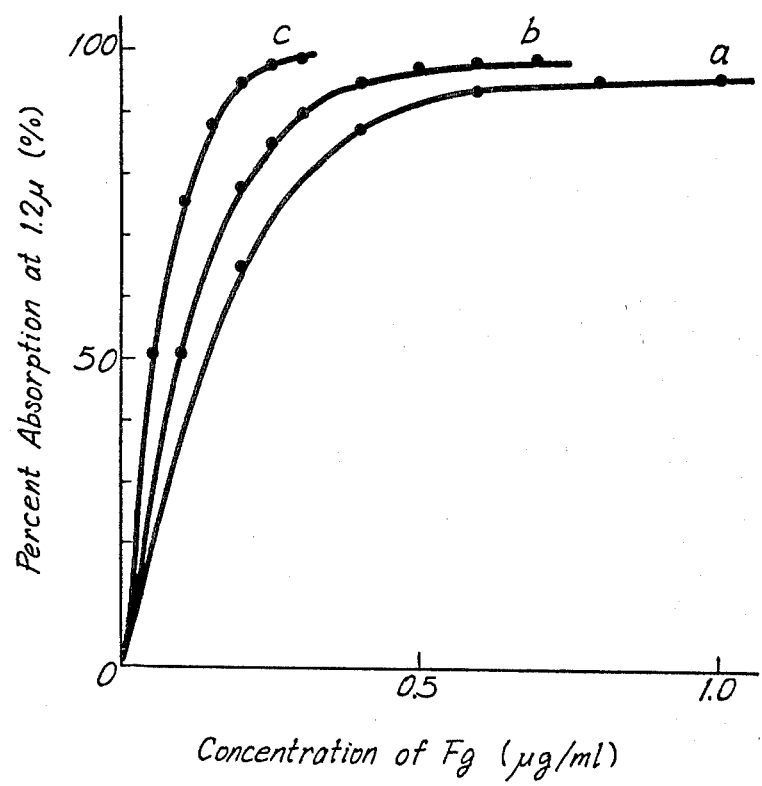
FIG. 12 is a graph which shows the change of detection sensitivity with concentration of anti-Fg-sensitized polystyrene latex.

Anti-Fg-sensitized latex reagents containing the anti-Fg-sensitized latex particles at concentrations of 0.75%, 1.0% and 2.0% by weight, respectively, are prepared in the same manner as described in Example 1, Part (1), except for use of another polystyrene latex with an average particle diameter of 0.35 micron. With each anti-Fg-sensitized latex reagent thus prepared, a standard curve is prepared in the same manner as described in Example 1, Part (2) (wavelength of the applied light 1.2 microns; shaking time 10 minutes). These standard curves are shown in FIG. 12, in which Curves a, b and c denote the standard curves obtained at concentrations of the anti-Fg-sensitized latex particles of 0.75, 1.0 and 2.0% by weight, respectively. As is evident from FIG. 12, the detection sensitivity for Fg increases as the concentration of the sensitized latex particles in the anti-Fg-sensitized latex reagent becomes higher.

EXAMPLE 11

An anti-Fg-sensitized latex reagent (concentration of latex particles: 0.5% by weight) is prepared in the same manner as described in Example 1, Part (1), except for use of another polystyrene latex having an average diameter of 0.804 micron.

A 0.2 ml aliquot of the Anti-Fg-sensitized latex reagent thus obtained is mixed with 0.2 ml of each of standard Fg solutions at different concentrations indicated in Table-O below, and the mixture is placed in a rectangular absorption cell having a thickness of 2 mm and stirred with an L-shaped stirring rod moving up and down at a speed of 160 strokes per minute in the cell to effect the antigen-antibody reaction. After 3 minutes, the absorbance of the reaction mixture is measured with light of a wavelength of 0.9 micron. The results are summarized in Table-O.

Table-O

| Concentration of standard Fg solution ($\mu$g/ml) | Absorbance after 3 min. |
| --- | --- |
| 0.0625 | 0.006 |
| 0.125 | 0.011 |
| 0.25 | 0.034 |
| 0.50 | 0.041 |
| 1.0 | 0.081 |
| 2.0 | 0.130 |

Figure 13:
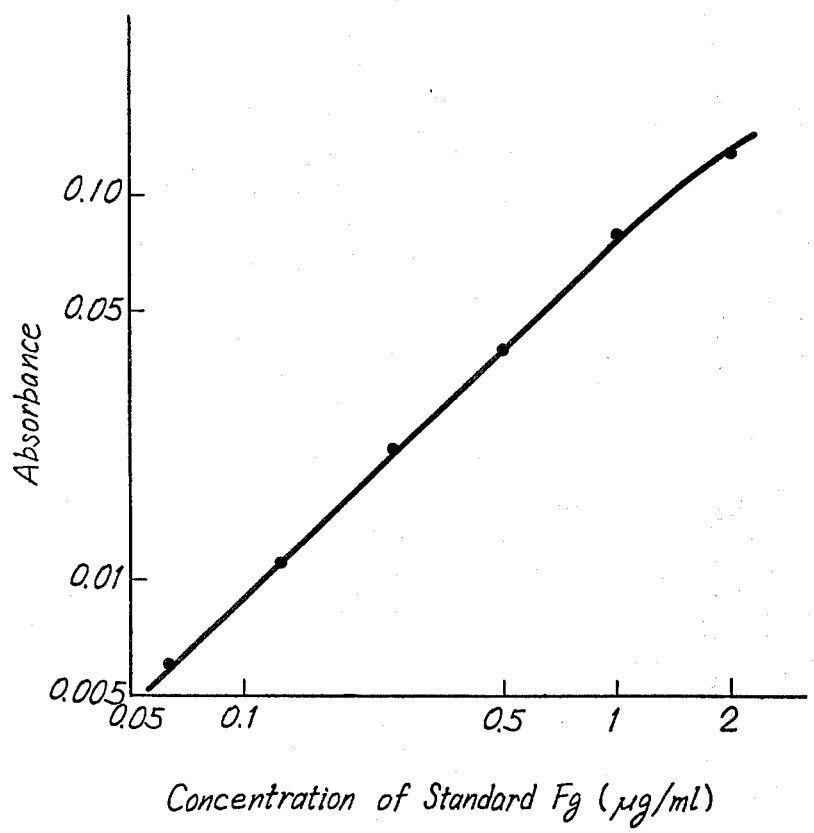
FIG. 13 shows a calibration curve of absorbance at 0.9 micron obtained by reacting an anti-Fg-sensitized latex reagent with each of standard Fg solutions at different concentrations.

When the above data are plotted graphically with concentration of standard Fg solution as abscissa and absorbance after 3 minutes as ordinate, a clear linear relationship is obtained as shown in FIG. 13.

EXAMPLE 12

An anti-hCG-sensitized latex reagent (containing 0.3% by weight latex particles) is prepared in the same manner as described in Example 1, Part (1), except that the anti-(human fibrinogen)antibody is replaced by anti-(human chorionic gonadotropin)antibody (anti-hCG) and the polystyrene latex of an average diameter of 0.481 micron by another polystyrene latex of an average diameter of 1.09 microns (Dow Chemical Co.). A 0.2 ml aliquot of the resulting anti-hCG-sensitized latex reagent is thoroughly mixed with 0.2 ml of each of standard hCG solutions having different concentrations indicated in Table-P below, and the mixture is placed in a rectangular absorption cell of 2 mm in thickness and stirred therein with an L-shaped stirring rod moving up and down at a speed of 160 strokes per minute to effect the antigen-antibody reaction. Accurately after 2 minutes, the absorbance of the reaction mixture is measured at 1.10 microns in wavelength of the applied light. The results are summarized in Table-P.

Table-P

| Concentration of standard hCG solution (IU/ml) | Absorbance after 2 min. |
| --- | --- |
| 0.0625 | 0.018 |
| 0.125 | 0.023 |
| 0.25 | 0.035 |
| 0.5 | 0.050 |

Table-P-continued

| Concentration of standard hCG solution (IU/ml) | Absorbance after 2 min. |
| --- | --- |
| 1.0 | 0.075 |

Figure 14:
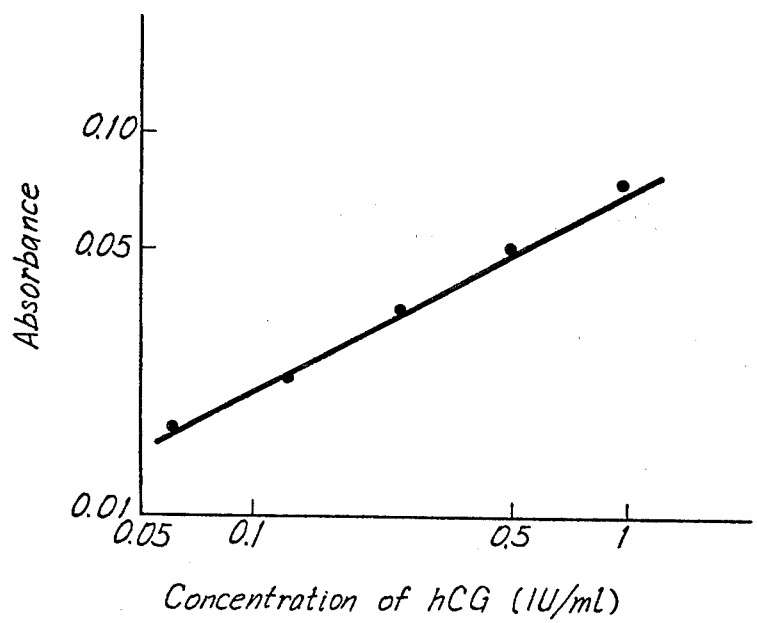
FIG. 14 shows a calibration curve of absorbance at 1.10 microns obtained by reacting an anti-hCG-sensitized latex reagent with each of standard hCG solutions at different concentrations.

When the above data are plotted on log-log graph paper with concentration of standard hCG solution as abscissa and absorbance after 2 minutes as ordinate, a calibration curve which assumes a clear straight line is obtained as shown in FIG. 14.

Having now fully described the invention, it will be apparent to one of ordinary skill in the art that many changes and modifications can be made thereto without departing from the spirit or scope of the invention as set forth herein.

What is claimed as new and intended to be covered by Letters Patent of the United States is:

1. An absorption method for determining antigens and antibodies comprising reacting an antigen or antibody or a mixture thereof with a corresponding antibody, or antigen or mixture thereof which has been supported on insoluble carrier particles having an average diameter of not greater than 1.6 microns to sensitize the carrier particles, said reaction being carried out in a liquid medium, wherein said carrier particles are present in the reaction mixture in a concentration of 0.05 to 1% by weight, irradiating the resulting reaction mixture with light having a wavelength in the range of 0.6 to 2.4 microns and longer than the average diameter of the carrier particles by a factor of at least 1.1 and measuring the absorbance or percent absorption of the reaction mixture.

2. The method according to claim 1 wherein the insoluble carrier particles used have an average diameter in the range of 0.1 to 1.0 micron.

3. The method according to claim 2 wherein the insoluble carrier particles used have an average diameter in the range of 0.2 to 0.8 micron.

4. The method according to claim 1 wherein said carrier particles consist essentially of fine powder of an organic high molecular substance or an inorganic substance which is substantially insoluble in the liquid medium.

5. The method according to claim 4 wherein said fine powder of the organic high molecular substance is a finely pulverized synthetic resin, bacteria or cell membrane fragments.

6. The method according to claim 4 wherein said fine powder of the organic high molecular substance is polystyrene latex particles.

7. The method according to claim 4 wherein said fine powder of the inorganic substance consists of at least one substance selected from the group consisting of metals, inorganic oxides or minerals.

8. The method according to claim 4 wherein said fine powder of inorganic substance consists of silica, alumina or silica-alumina.

9. The method according to claim 1 wherein the reaction of said antibody- or antigen-sensitized insoluble carrier particles with said antigen or antibody or a mixture thereof is carried out under conditions that accelerate contact of the carrier particles with each other as much as possible.

10. The method according to claim 1 wherein the reaction of said antibody- or antigen-sensitized insoluble carrier particles with said antigen or antibody or a mixture thereof is carried out under predetermined conditions which accelerate contact of the carrier particles with each other and the absorbance or percent absorption of the resulting reaction mixture is measured.

11. The method according to claim 9 or 10 wherein said reaction is carried out with agitation.

12. The method according to claim 1 wherein the amount or concentration of an antigen or antibody or both in a sample solution is determined by reacting the antigen, antibody or both in the sample solution with the corresponding antibody or antigen or mixture thereof supported on said carrier for a given period of time under predetermined conditions, and measuring the absorbance or percent absorption of the resulting reaction mixture.

13. The method according to claim 1 wherein the amount or concentration of an antigen or antibody or both in a sample solution is determined by reacting the antigen, antibody or both in the sample solution with the corresponding antibody or antigen or mixture thereof supported on said carrier under predetermined conditions, and measuring the length of time required for the absorbance or percent absorption of the reaction mixture to reach a predetermined value.

14. The method according to claim 1 wherein the light applied has a wavelength in the range of 0.8 to 1.8 microns.

15. The method according to claim 14 wherein the light applied has a wavelength in the range of 0.9 to 1.4 microns.

16. The method according to claim 1 wherein the light applied has a wavelength longer than the average diameter of the carrier particles by a factor of at least 1.5.

17. The method according to claim 1 wherein a reaction mixture resulting from an antigen or antibody or a mixture thereof present in a sample solution and the corresponding antibody or antigen or mixture thereof supported on a carrier having a particular particle size is irradiated with light having an appropriate wavelength in the range of 0.6 to 2.4 microns in order to previously detect the wavelength region in which a certain correlation is established between the concentration of the antigen or antibody or a mixture thereof, including the reaction product, in the sample solution and the absorbance or percent absorption of the reaction mixture, and the measurement of the absorbance or percent absorption is conducted by irradiating the reaction mixture with light of a wavelength in such region.

18. The method according to claim 1 wherein said carrier particles are used in such a proportion that the concentration of the carrier in the reaction mixture is 0.2 to 0.6% by weight.

19. The method according to claim 1 wherein said liquid medium is water or a mixture of water and a water-miscible organic solvent.

20. The method according to claim 1 wherein a diluted or undiluted sample solution containing an antigen or antibody is reacted with a suspension of the carrier particles on which a particular antibody or antigen has been supported.

21. The method according to claim 1 wherein at first an antigen or antibody is added to and reacted with a sample solution containing an antibody or antigen to be measured and subsequently a suspension of the insoluble carrier particles on which a particular antigen or antibody has been supported is added to and reacted with the reaction mixture of the first reaction.

22. The method according to claim 1 wherein the antibody or antigen is supported on said insoluble carrier particles by physical or chemical adsorption or a mixture of both thereon.

23. The method according to claim 1 wherein the antibody or antigen is supported on said insoluble carrier particles by chemical bonding therewith by the use of a coupling agent.

24. An apparatus for measuring antigens and antibodies which comprises:
an adsorption cell holding the reaction mixture obtained by reacting an antibody or antigen supported on insoluble carrier particles having an average diameter of not greater than 1.6 microns, with a corresponding antigen or antibody or mixture thereof in a liquid medium, said cell having a thickness of 0.5 to 10 mm; and said cell being in a photometer for the measurement of absorbance or percent absorption which comprises an irradiation unit for applying light of a particular wave length to the cell and a detection unit for measuring the light absorbed by said cell; wherein said wave length is selected from the range of from 0.6 to 2.4 microns.

25. The apparatus according to claim 24 wherein the insoluble carrier particles have an average diameter in the range of 0.1 to 1.0 micron.

26. The apparatus according to claim 26 wherein the insoluble carrier particles have an average diameter in the range of 0.2 to 0.8 micron.

27. The apparatus according to claim 24 wherein the thickness of the cell is from 1 to 5 mm.

28. The apparatus according to claim 24 wherein the walls of the cell which transmit the light are composed of transparent glass or synthetic resin having at least 30% transmittance for light of 0.6 to 2.4 microns.

29. The apparatus according to claim 24 wherein the photometer involves an irradiation unit for applying light of a particular wavelength selected from the range of 0.8 to 1.8 microns.

30. The apparatus according to claim 24 wherein the cell is equipped with an agitator.

31. The apparatus according to claim 30 wherein the agitator comprises a mixing rod moving in the cell.

* * * * *